United States Patent [19]

Bellussi et al.

[11] Patent Number: 5,049,536

[45] Date of Patent: Sep. 17, 1991

[54] CATALYTICALLY ACTIVE SILICA AND ALUMINA GEL AND PROCESS FOR PREPARING IT

[75] Inventors: Giuseppe Bellussi, Piacenza; Mario G. Clerici, San Donato Milanese; Angela Carati, San Giuliano Milanese; Fabrizio Cavani, Modena, all of Italy

[73] Assignee: Eniricerche S.p.A., Milan, Italy

[21] Appl. No.: 345,142

[22] Filed: Apr. 28, 1989

[30] Foreign Application Priority Data

May 6, 1988 [IT] Italy ............................... 20494 A/88

[51] Int. Cl.$^5$ ............................................. B01J 21/12
[52] U.S. Cl. ..................................... 502/235; 502/263
[58] Field of Search ........................ 502/235, 238, 263

[56] References Cited

U.S. PATENT DOCUMENTS

| | | | |
|---|---|---|---|
| 3,535,232 | 10/1970 | Lawrance et al. | 502/235 |
| 3,923,691 | 12/1975 | Braithwaite et al. | 502/238 |
| 4,766,101 | 8/1988 | Nortier et al. | 502/263 |

FOREIGN PATENT DOCUMENTS 225407  6/1987  European Pat. Off. ............ 502/263

*Primary Examiner*—Carl F. Dees
*Attorney, Agent, or Firm*—Hedman, Gibson, Costigan & Hoare

[57] ABSTRACT

A silica and alumina gel is disclosed, which is amorphous at X-rays, has a molar ratio of $SiO_2/Al_2O_3$ comprised within the range of from 30/1 to 500/1, a surface area comprised within the range of from 500 to 1000 m$^2$/g, a total volume of pores comprised within the range of from 0.3 to 0.6 ml/g, an average diameter of the pores of the order of magnitude of 10 Å or less and which is free, or substantially free, from pores having a diameter larger than 30 Å.

Such a silica and alumina gel is catalytically active in reactions of conversion of the hydrocarbons, such as: oligomerization, alkylation, isomerization and dewaxing.

Also a process for preparing such a silica and alumina gel is disclosed.

12 Claims, 1 Drawing Sheet

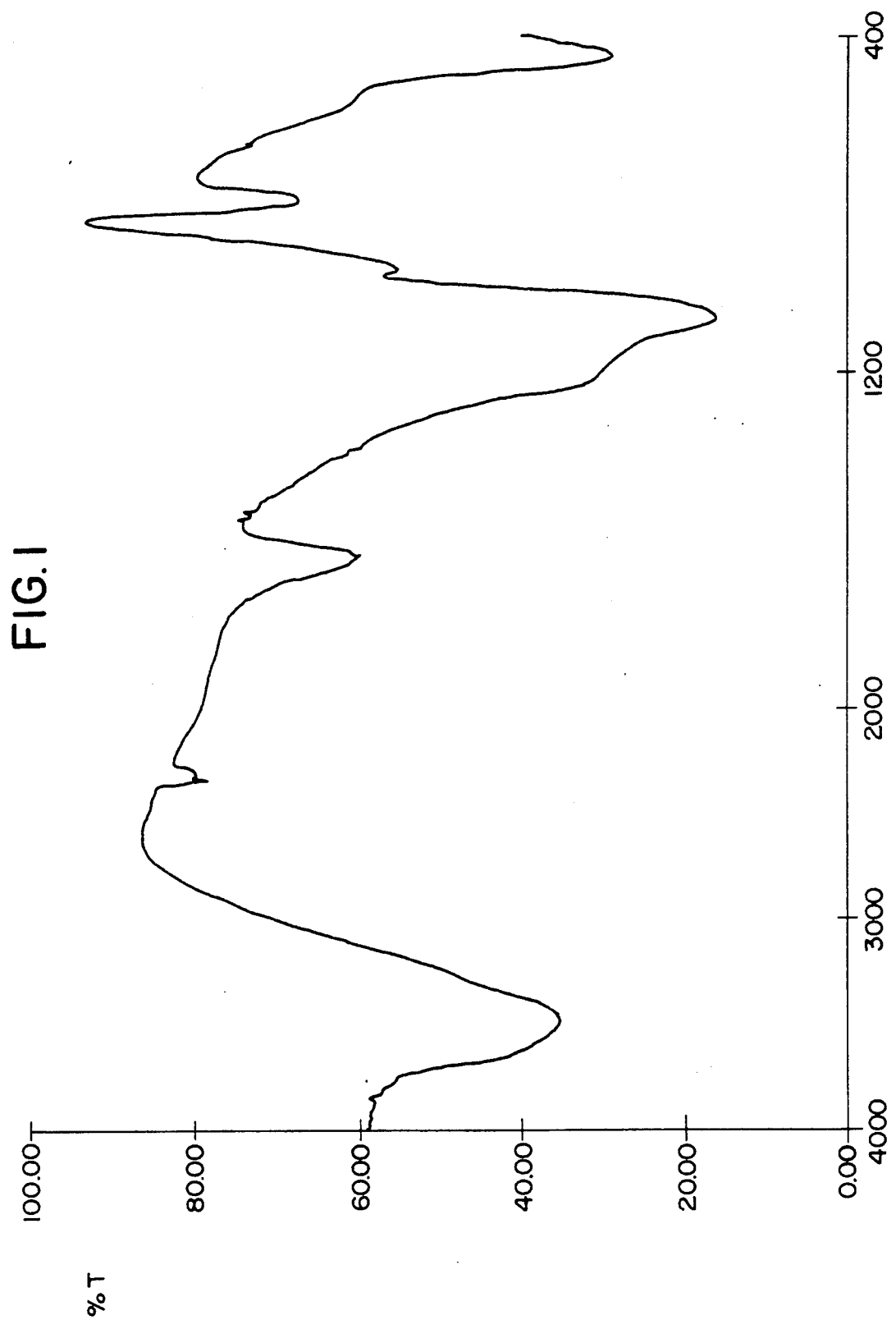

CATALYTICALLY ACTIVE SILICA AND ALUMINA GEL AND PROCESS FOR PREPARING IT

The present invention relates to a catalytically active silica and alumina gel and to a process for preparing it.

The invention relates also to the use of such a silica and alumina gel as a catalyst in hydrocarbon conversion processes.

In the art, the use is known of zeolites in processes os separation by adsorption and the like, or as catalysts in various reactions of conversion of hydrocarbons. These zeolites, also known as molecular sieves, are aluminosilicates of either natural or synthetic origin, of crystalline nature. For this known art, reference is made to the review in Kirk-Othmer "Encyclopaedia of Chemical Technology", Third Edition, Volume 15, pages 638–669.

In the art also some gels of silica and alumina, of amorphous nature, were described, which are endowed with catalytic activity. So, for example, European patent application Publ. N. 160,145 discloses a process of alkylation of aromatic hydrocarbons which uses a catalyst constisting of a silica and alumina gel, of amorphous nature, which has a diamater of the pores which is typically comprised within the range for from 50 to 500 Å and with a ratio of silica to alumina which is typically comprised within the range of from 1/1 to 10/1. M.R.S. Manton and J.C. Davidtz in Journal of Catalysis, 60, 156–166 (1979) describe a process for the synthesis of amorphous catalysts of silica and alumina having a controlled volume of the pores, with these catalysts typically having pores with a diameter comprised within the range of from 3.7 to 15 mm (from 37 to 150 Å).

The present Applicant found now a microporous, catalytically active silica and alumina gel, amorphous at X-rays and capable of showing unexpectedly good values of selectivity to the useful reaction products in hydrocarbon conversion processes.

In accordance therewith, the present invention relates to a silica and alumina gel, which is amorphous at X-rays, has a molecular ratio of $SiO_2/Al_2O_3$ comprised within the range of from 30/1 to 500/1, a surface area comprised within the range of from 500 to 1000 $m^2/g$, a total volume of pores comprised within the range of from 0.3 to 0.6 ml/g, an average diameter of the pores of the order of magnitude of 10 Å or less and which is free, or substantially free, from pores having a diameter larger than 30 Å, obtained by:

(a) preparing an aqueous solution of tetra-alkyl-ammonium hydroxide (TAA-OH) in which the alkyl is selected from among ethyl, n.-propyl and n.-butyl, a of soluble compound of aluminum capable of yielding $Al_2O_3$: by hydrolysis and of a soluble silicon compound capable of yielding $SiO_2$ by hydrolysis; with the amount of the constituents of the solution being such as to comply with the following molar ratios:

| | |
|---|---|
| $SiO_2/Al_2O_3$ | from 30:1 to 500:1; |
| TAA—OH/$SiO_2$ | from 0.05:1 to 0.2:1; |
| $H_2O/SiO_2$ | from 5:1 to 40:1; |

(b) heating the so-obtained solution in order to cause the gelification to occur;
(c) drying the obtained gel; and
(d) calcining the dried gel, operating first under an inert atmosphere and then under an oxidating atmosphere.

The use of tetra-ethyl-ammonium, tetra-n.-propyl-ammonim, or tetra-n.-butyl-ammonium hydroxide in the (a) step of the present process is critical. In fact, the use of similar ammonium compounds, such as tetra-methyl-ammonium hydroxide, leads to the formation of silica and alumina gels which containing mesopores (having a pore size larger than 30 Å), which are not catalytically active, or show a poor catalytic activity.

The preferred soluble aluminum compounds useable in the (a) step of the present process are aluminum trialkoxides, such as, e.g., aluminum tri-n.-propoxide and aluminum tri-isopropoxide.

The preferred soluble silicon compounds useable in the (a) step of the present process are the tetraalkyl silicates, such as, for example, tetra-ethyl silicate. The (a) step of the process is carried out at room temperature (20°–25° C.), or at temperatures higher than room temperature, up to values close to those at which the gelification begins (about 50° C.).

The order of addition of the constituents of the solution in the (a) step is not critical.

However, an aqueous solution should be preferably formed initially, which contains the tetra-alkyl-ammonium hydroxide and the soluble aluminum compound, with the soluble silicon compound being :hen added to aid solution.

In any case, in the resulting solution the following molar ratios should be complied with:

| | |
|---|---|
| $SiO_2/Al_2O_3$ | from 30:1 to 500:1 |
| TAA—OH/$SiO_2$ | from 0.05:1 to 0.2:1 |
| $H_2O/SiO_2$ | from 5:1 to 40:1 |
| The preferred values for such ratios are: | |
| $SiO_2/Al_2O_3$ | from 50:1 to 300:1 |
| TAA—OH/$SiO_2$ | from 0.05:1 to 0.2:1 |
| $H_2O/SiO_2$ | from 10:1 to 25:1 |

The gelification in the (b) step of the present process is carried out by heating the solution at a temperature comprised within the range of from 50° C. to 70° C., and preferably of the order of 60° C. The necessary time for the gelification to be completed varies as a function of temperature, of the concentrations, or of still other parameters, and is normally comprised within the range of from 15 minutes up to 5 hours, and is typically comprised within the range of from 25 to 60 minutes. Carrying out the gelification by means of a simple heating of the solution is critical.

In fact, by operating under acidic conditions, as in the prior art, silica and alumina gels are obtained which have undesired characteristics, in particular as regards the porosities and the distribution of the size of the pores.

The so-obtained gel is submitted to drying in the (c) step of the process according to the present invention. Such a drying is suitably carried out at temperatures of up to about 150° C., and preferably of the order, of 90°–100° C., for a long enough time in order to eliminate water to a complete or substantially complete extent.

According to a form of practical embodiment of the present invention, the drying of the (c) step is carried out by spray-drying. In this case, a spray-drying apparatus can be used, in which the gel is injected as droplets which are put into contact with an inert gas, operating at a gas inlet temperature of the order of 230°–250° C., and with a gas outlet temperature of the order to 140°–160° C.

In any cases, the dried gel is submitted to a treatment of calcination, in the (d) step of the present invention, and said treatment is suitably carried out first under an inert atmosphere, for example under nitrogen, and then under an oxidating atmosphere, for example in air. The calcination temperatures are suitably comprised within the range of from 500° to 700° C., and preferably are of the order of 550°–600° C. The calcination times may vary within the range of from 4 to 20 hours, and typically are of the order of 6–16 hours.

In this way, a silica and alumina gel is obtained, according to the present invention, which shows a structure completely amorphous at X-rays, and a value of the ratio of $SiO_2/Al_2O_3$ which is the same as the one which derives from the initially charged compounds of silicon and aluminum, and is comprised within the range of from 30:1 to 500:1, and preferably of from 50:1 to 300:1.

Such a silica and alumina gel has a large surface area, with the values of the specific surface area thereof (BET determination) being comprised within the range of from 500 to 1000 $m^2/g$. The total volume of the pores is comprised within the range of from 0.3 to 0.6 ml/g. The pores have sizes within the range of micropores, with their average diameter being of the order of 10 Å or less, and with their size distribution being narrow. In particular, pores having a diameter larger than 30 Å are absent or virtually absent, and in general pores having a diameter larger than 20 Å are absent.

The silica and alumina gel according to the present invention is catalytically active in the processes of conversion of hydrocarbons. For such an use, it can be used as such, or it can be used in combination with suitable metal oxides acting as binding agents. Suitable oxides which can be used for the intended purpose are silicas, aluminas and titanium, magnesium and zirconium oxides. The silica and alumina gel and the binding agent can be mixed according to weight ratios comprised within the range of from about 50:50 up to 95:5, and preferably comprised within the range of from 70:30 to 90:10. The two components can be mixed by means of traditional mixing techniques, and the obtained blend can be compacted to the desired end shape, e.g., as extruded shapes, or as granulates. By operating in this way, the catalyst can be given better mechanical characteristics.

The reactions which are catalysed by the silica-alumina gel according to the present invention are the reactions of dimerization of olefins, in particular of the linear olefins with a chain length of from 4 to 15 carbon atoms; of isomerization, for example of butenes isomerizations; of alkylation of the hydrocarbons with olefins and of dewaxing. If these reactions, the catalysts according to the present invention show a good activity and, above all, a high selectivity to the useful reaction products.

The following experimental examples are reported in order to better illustrate the present invention.

EXAMPLE 1

In 50 g of tetra-n.-propyl-ammonium hydroxide (TPA-OH) at 30.6% by weight 1.4 g of aluminum tripropoxide [Al(O-n.-$C_3H_7$)$_3$]is dissolved, and 56 g of demineralized water is subsequently added.

These operations are carried out at room temperature (about 20° C.).

The so-obtained solution is heated up to 60° C. and then 104 g of tetra-ethyl-silicate (TES) is added with stirring.

In the so-obtained mixture, in which the following molar ratios have the following values:

$SiO_2/Al_2O_3 = 145:1;$
$TPA-OH/SiO_2 = 0.15:1;$
$H_2O/SiO_2 = 10:1.$

The mixture is kept stirred at 60° C., and 30 minutes later a homogeneous gel is obtained, which is dried inside a rotavapor, under an air stream, with the termoregulated bath being kept at the temperature of 90° C., and then inside an oven at 100° C.

The dried gel is calcined at 600° C. for 3 hours, under a nitrogen stream and then for 10 hours under an air stream.

Thirty g is obtained of a silica-alumina gel, with a quantitative yield relatively to the initially charged silicon and aluminum.

The chemical analysis confirms that the molar ratio of $SiO_2/Al_2O_3$ has the same value as of the reaction mixture, after the charging of the reactants.

The X-ray diffraction of the powders, by means of a vertical Philips goniometer using the CuKα radiation confirms the completely amorphous nature of the gel of silica and alumina.

The spectrum of the gel, recorded by means of an I.R. spectroscopic analysis, carried out by means of FTIR-1730 spectrometer manufactured by Perkin Elmer, is reported in FIG. 1.

The surface area of the gel, measured by means of Carlo Erba's Sorptomatic 1800 resulted to be of 800 $m^2/g$.

The porosity of the gel is of 0.44 ml/g, with no pores of more than 20 Å of diameter being present, and with the average diameter of its pores being of $\leq 10$Å.

These last two determinations are carried out by means of Carlo Erba's instrument Sorptomatic 1800.

EXAMPLE 2

To 27 g of TPA-OH at 30% by weight 2 g of aluminum tripropoxide is added, and after the dissolution of this latter, 85 g of demineralized water is added.

The so-obtained solution is heated from 20° C. up to 60° C. and then 104 g of TES is added.

In the so-obtained mixture, in which the following molar ratios have the following values:

$SiO_2/Al_2O_3 = 102;$
$TPA-OH/SiO_2 = 0.08;$
$H_2O/SiO_2 = 11.5.$

The mixture is kept stirred at 60° C. until a clear and compact gel is obtained (the necessary time is of about 30 minutes), and said gel is dried first inside a rotavapor, and then inside an oven at 100° C. for 1 hour.

The calcination is then carried out at 550° C. for 1 hour under a nitrogen stream and then for 5 further hours under an air stream.

27 g is obtained of a silica-alumina gel, which has the above indicated ratio of $SiO_2/Al_2O_3$, is completely amorphous at X-rays, has a surface area of 658 $m^2/g$, with a porosity of 0.46 ml/g, with no pores of more than 20 Å of diameter being present, and with the average diameter of its pores being of $\leq 10 \text{Å}$.

EXAMPLE 3

Operating at room temperature (about 20° C.), a clear solution is prepared by dissolving 2 g of aluminum-tri-propoxide in 40.5 g of TPA-OH at 25% by weight, and then adding 146 g of demineralized water.

The solution is heated up to 60° C. and then 104 g of TES is added. A mixture is obtained, in which the following molar ratios have the following values:

$SiO_2/Al_2O_3 = 102$;
$TPA-OH/SiO_2 = 0.10$;
$H_2O/SiO_2 = 21$.

The mixture is kept stirred at 60° C. for about 1 hour, until a homogeneous gel is obtained. This gel is left standing for 50 hours at room temperature (about 20° C.), then is dried inside a rotavapor, under atmospheric pressure, under a slightly flowing air stream, with the temperature-controlled bath being kept at 90° C. The gel is finally dried for 1 hour at 150° C. and is calcined at 550° C. for 3 hours under a nitrogen stream and for 13 hours at 600° C. under an air stream.

30 g is obtained of a silica-alumina gel, which has the above indicated ratio of $SiO_2/Al_2O_3$, is completely amorphous at X-rays, has a surface area of 760 m$^2$/g, a porosity of 0.44 ml/g, and does not contain pores of more than 20 Å of diameter, with the average diameter of its pores being of $\leq 10 \text{Å}$.

EXAMPLE 4

Operating at room temperature (about 20° C.), 2 g of aluminum-tri-propoxide is dissolved in 51 g of TPA-OH at 30% by weight, and then 180.0 g of demineralized water is added.

The solution is heated up to 60° C. and then 104.2 g of TES is added. A mixture is obtained, in which the following molar ratios have the following values:

$SiO_2/Al_2O_3 = 102$;
$TPA-OH/SiO_2 = 0.15$;
$H_2O/SiO_2 = 24$.

The mixture is kept stirred at 60° C. for about 4 hours, is left standing for 11 days at room temperature (about 20° C.), then is spray-dried by using a flow rate of 4.5 ml of gel per minute, with the gas fed to the drier having an inlet temperature of 240° C. and an outlet temperature of 150° C. The dried gel is calcined at 550° C. for 1 hour under a nitrogen stream and for 5 hours under an air stream.

29 g is obtained of a silica-alumina gel, with the above indicated ratio of $SiO_2/Al_2O_3$, which is completely amorphous at X-rays, has a surface area of 541 m$^2$/g, and a porosity of 0.47 ml/g; it does not contain pores of more than 20 Å of diameter and its average pore diameter is of $\leq 10 \text{Å}$.

EXAMPLE 5

Operating at room temperature (about 20° C.), 0.68 g of aluminum-tri-propoxide is dissolved in 50 g of TPA-OH at 30.6% by weight. To this solution, 56 g of demineralized water is added, and after being heated to 50° C., to it 104 g of TES is added.

A mixture is obtained, in which the following molar ratios have the following values:

$SiO_2/Al_2O_3 = 300$;
$TPA-OH/SiO_2 = 0.15$;
$H_2O/SiO_2 = 10$.

The mixture is kept stirred at 50° C. for 1.5 hours, until a clear and compact gel is obtained, which is dried first for 3 hours inside the rotavapor at the controlled temperature of 80° C., and then for 1 hour inside an oven at 120° C.

The dried gel is finally calcined at 600° C. for 3 hours under a nitrogen stream and for 7 hours under an air stream.

30 g is obtained of a silica-alumina gel, which has the above indicated ratio of $SiO_2/Al_2O_3$, is completely amorphous at X-rays, has a surface area of 974 m$^2$/g, has a porosity of 0.45 ml/g, is free from pores of more than 20Å of diameter, and with the average diameter of its pores being of $\leq 10 \text{Å}$.

EXAMPLE 6

Operating at room temperature (about 20° C.), 4 g of aluminum-tri-propoxide is dissolved in 48.5 g of TPA-OH at 25% by weight. To this solution, 170 g of water is added, and after, being heated to 60° C., to it 104 of TES is added.

A mixture is obtained, in which the following molar ratios have the following values:

$SiO_2/Al_2O_3 = 51$;
$TPA-OH/SiO_2 = 0.12$;
$H_2O/SiO_2 = 23$.

The mixture is kept stirred at 60° C. for 25 minutes, until a clear and compact gel is obtained, which is kept standing for 10 hours at room temperature, then is dried for 3 hours inside the rotavapor. In an air stream, with the thermoregulated bath being kept at the controlled temperature of 90° C., and then inside an oven at 100° C.

The dried gel is finally calcined at 600° C. for 3 hours under a nitrogen stream and for 13 hours under an air stream.

28 g is obtained of a silica-alumina gel, with the above indicated ratio of $SiO_2/Al_2O_3$, which has a surface area of 810 m$^2$/g, has a porosity of 0.44 ml/g, is free from pores of more than 20 Å of diameter, and with the average diameter of its pores being of $\leq 10 \text{Å}$.

EXAMPLE 7 (COMPARATIVE EXAMPLE)

The process is carried out in the same way as in Example 1, with tetramethyl-ammonium hydroxide (TMA-OH) being used instead of TPA-OH.

After the addition of TES, a mixture with the following values of the molar ratios is obtained:

$SiO_2/Al_2O_3 = 145$;
$TMA-OH/SiO_2 = 0.15$;
$H_2O/SiO_2 = 10$.

29 g is obtained of a silica-alumina gel, which has the above indicated ratio of $SiO_2/Al_2O_3$, is completely amorphous at X-rays, has a surface area of 231 m$^2$/g, has a porosity of 0.44 ml/g, with the average diameter of its pores being comprised within the range of from ≦10 up to 100Å.

EXAMPLE 8

The process is carried out in the same way as in Example 1, with tetra-ethyl-ammonium hydroxide (TEA-OH) being used instead of TPA-OH.

After the addition of TES, a mixture with the following values of the following molar ratios is obtained:

$SiO_2/Al_2O_3 = 145$;
$TEA-OH/SiO_2 = 0.15$;
$H_2O/SiO_2 = 10$.

A silica-alumina gel is obtained with a quantitative yield with the above indicated ratio of $SiO_2/Al_2O_3$, which is completely amorphous at X-rays, has a surface area of 539 m²/g, has a porosity of 0.40 ml/g, is free from pores of diameter larger than 30Å, and with an average diameter of the pores of about ≦10Å.

EXAMPLE 9

The process is carried out in the same way as in Example 1, with tetra-butyl-ammonium hydroxide (TBA-OH) being used instead of TPA-OH.

After the addition of TES, a mixture with the following values of the following molar ratios is obtained:

$SiO_2/Al_2O_3 = 145$;
$TBA-OH/SiO_2 = 0.15$;
$H_2O/SiO_2 = 10$.

30 g is obtained of a silica-alumina gel with the above indicated ratio of $SiO_2/Al_2O_3$, which is completely amorphous at X-rays, has a surface area of 929 m²/g, has a porosity of 0.45 ml/g, is free from pores of diameter larger than 20 Å, and with an average diameter of its pores of about ≦10Å.

EXAMPLE 10

Some gels from the silica and alumina gels prepared in the preceding Examples are used as catalysts for the dimerization of linear olefins, selected from among:
(a) a mixture of linear isomers of tetradecene;
(b) 7-tetradecene (a product by Aldrich; purity 98%);
(c) 1-octene,
previously purified by distillation through a 20-tray distillation tower.

Going into details, the dimerization tests are carried out according to the following procedure. 0.2–0.4 g of catalyst and 6 ml of olefin are charged to a small autoclave of pyrex glass. The mixture is heated with stirring at the desired temperature by means of a thermocontrolled bath. At the end of the reaction time, the reaction products are analysed by means of quantitative gas-chromatographic analysis. The nature of these products is confirmed by mass spectrometry. In following Table 1, the reaction conditions are reported together with the percent yield to dimers and trimers. The remaining percentage is constituted by linear isomers of the starting olefins.

TABLE 1

| Catalyst of Example N. | Catalyst (g) | Olefin (ml) | Temperature (°C.) | Time (hours) | Dimers (% yield) | Trimers (% yield) |
|---|---|---|---|---|---|---|
| 1 | 0.4 | 6(a) | 200 | 2 | 30 | 4 |
| 1 | 0.4 | 6(b) | 200 | 3 | 44 | 5 |
| 2 | 0.4 | 6(a) | 200 |   | 32 | 5 |
| 2 | 0.4 | 6(b) | 200 | 3 | 48 | 9 |
| 3 | 0.4 | 6(b) | 175 | 3 | 15 | 1.5 |
| 3 | 0.4 | 6(b) | 200 | 1.5 | 48 | 9 |
| 3 | 0.2 | 6(c) | 150 | 3 | 32 | 3 |
| 4 | 0.2 | 6(b) | 200 | 5 | 43 | 6 |

We claim:

1. Silica and alumina gel, which is amorphous at X-rays, has a molecular ratio of $SiO_2/Al_2O_3$ comprised within the range of from 30/1 to 500/1, a surface area comprised within the range of from 500 to 1000 m²/g, a total volume of pores comprised within the range of from 0.3 to 0.6 ml/g, an average diameter of the pores of the order of magnitude of 10 Å or less and is free, or substantially free, from pores having a diameter larger than 30 Å, obtained by:

(a) preparing an aqueous solution of tetra-alkyl-ammonium hydroxide (TAA-OH) in which the alkyl is selected from among ethyl, n.-propyl and n.-butyl, of a soluble compound of aluminum capable of yielding $Al_2O_3$ by hydrolysis and of a soluble silicon compound capable of yielding $SiO_2$ by hydrolysis; with the amount of the constituents of the solution being such as to comply with the following values of the following molar ratios:

| $SiO_2/Al_2O_3$ | from 30:1 to 500:1; |
|---|---|
| $TAA-OH/SiO_2$ | from 0.05:1 to 0.2:1; |
| $H_2O/SiO_2$ | from 5:1 to 40:1; |

(b) heating the so-obtained solution in order to cause the gelification to occur;
(c) drying the obtained gel; and
(d) calcining the dried gel, by operating first under an inert atmosphere and then under an oxidating atmosphere.

2. Silica and alumina gel according to claim 1, characterized in that the soluble compound in the (a) step is aluminum tri-alkoxide and the soluble silicon compound in the (a) step is a tetra-alkyl silicate.

3. Silica and alumina gel according to claim 2, characterized in that said soluble aluminum compound is aluminum tri-n.-propoxide or aluminum tri-isopropoxide and said soluble silicon compound is tetra-ethyl silicate.

4. Silica and alumina gel according to claim 1, characterized in that the constituents of the solution in the (a) step are in such an amount as to comply with the following molar ratios:

| $SiO_2/Al_2O_3$ | from 50:1 to 300:1 |
|---|---|
| $TAA-OH/SiO_2$ | from 0.05:1 to 0.2:1 |
| $H_2O/SiO_2$ | from 10:1 to 25:1 |

5. Silica and alumina gel according to claim 1, characterized in that in said (a) step the reaction is carried out at a temperature comprised within the range of from room temperature (20°–25° C.) up to values close to those at which the gelification begins (about 50° C.).

6. Silica and alumina gel according to claim 1, characterized in that said gelification in the (b) step is carried out at a temperature comprised within the range of from 50° C. up to 70° C., for a time comprised within the range of from 15 minutes up to 5 hours.

7. Silica and alumina gel according to claim 6, characterized in that said gelification is carried out at a temperature of 60° C., for a time of the order of magnitude of 25–60 minutes.

8. Silica and alumina gel according to claim 1, characterized in that the (c) drying step is carried out at temperatures of up to 150° C.

9. Silica and alumina gel according to claim 8, characterized in that said (c) drying step is carried out at temperatures of the order of magnitude of 90°–100° C.

10. Silica and alumina gel according to claim 1, characterized in that said (c) drying step is carried out by spray-drying.

11. Silica and alumina gel according to claim 1, characterized in that the (d) calcination step is carried out at a temperature comprised within the range of from 500° to 700° C., for a time of from 4 to 20 hours.

12. Silica and alumina gel according to claim 11, characterized in that said (d) calcination step is carried out at about 550°–600° C., and for a time of about 6–16 hours.

* * * * *